United States Patent [19]

Carlos

[11] Patent Number: 4,533,458
[45] Date of Patent: Aug. 6, 1985

[54] REDOX CATALYST PLUS PROMOTER FOR OXIDATION OF HYDROCARBONS

[75] Inventor: Donald D. Carlos, Louisville, Ky.

[73] Assignee: Ashland Oil, Inc., Ashland, Ky.

[21] Appl. No.: 539,433

[22] Filed: Oct. 6, 1983

Related U.S. Application Data

[63] Continuation-in-part of Ser. No. 262,859, May 12, 1981, abandoned.

[51] Int. Cl.³ .................. C07C 53/00; C07C 27/10
[52] U.S. Cl. ............................. 208/3; 260/398.6
[58] Field of Search ..................... 260/398.6; 208/3

[56] References Cited

U.S. PATENT DOCUMENTS

| | | | |
|---|---|---|---|
| 1,983,672 | 12/1934 | Laborthe, Jr. ................... | 208/3 |
| 2,095,473 | 10/1937 | Keunecke ....................... | 196/126 |
| 2,156,266 | 5/1939 | Murphree ....................... | 568/954 |
| 2,216,222 | 10/1940 | Beller ............................ | 568/954 |
| 2,610,974 | 9/1952 | Nelson ........................... | 568/954 |
| 2,704,294 | 3/1955 | Morgan, Jr. ................... | 260/451 |
| 2,776,308 | 1/1957 | Nelson ........................... | 260/398.6 |
| 2,808,423 | 10/1957 | Bartlett et al. ................. | 208/3 |
| 2,837,553 | 6/1958 | Ferris ............................ | 208/5 |
| 4,199,431 | 4/1980 | Carlos ........................... | 208/3 |
| 4,390,472 | 6/1983 | Hanotier et al. ............... | 208/3 |
| 4,426,329 | 1/1984 | Woods et al. .................. | 208/3 |

*Primary Examiner*—D. E. Gantz
*Assistant Examiner*—Helane Myers
*Attorney, Agent, or Firm*—Richard C. Willson, Jr.

[57] ABSTRACT

Liquid hydrocarbons are oxidized in the presence of a redox catalyst metal in combination with an alkali metal or alkaline metal promoter.

2 Claims, No Drawings

REDOX CATALYST PLUS PROMOTER FOR OXIDATION OF HYDROCARBONS

BACKGROUND OF THE INVENTION

This is a continuation-in-part of Ser. No. 262,859, filed May 12, 1981 now abandoned, incorporated herein by reference.

The present invention relates to the oxidation of hydrocarbons. More specifically, the present invention relates to the oxidation of hydrocarbon waxes and petrolatums. Oxidized petroleum fractions including waxes and petrolatums have, in the past, been employed as the source of saponifiable material in the production of lubricating greases and in the formulation of protective coatings. The oxidates employed for these purposes have been obtained by oxidizing selected petroleum fractions under controlled conditions such that the oxidation proceeds only to a limited extent.

Oxidation of petroleum fractions by the above-described method had, associated with it, certain difficulties. Some petroleum fractions are not easily oxidized by the prior art processes and even though oxidizable, in some instances, require a preliminary induction period before the rate of oxidation becomes appreciable. Another problem associated with oxidizing petrolatums is the discoloration of the final wax product rendering it aesthetically unattractive for use in some formulations.

Other problems involve the presence of various oxidation inhibitors and/or redox catalyst poisons in the hydrocarbon fraction. These oxidation inhibitors and/or redox catalyst poisons are often nitrogen and/or sulfur-containing compounds present as impurities in the hydrocarbon source.

To overcome the above problems, the prior art suggests the employment of various oxidation catalysts, such as redox catalysts with or without promoters, for use in the hydrocarbon oxidation process. The redox catalysts are often based on expensive redox metals, such as manganese, chromium and the like.

The redox catalysts used in the present invention are known in the prior art to be useful in the oxidation of hydrocarbon waxes and petrolatums. For example, U.S. Pat. No. 1,983,672 by Labarthe, Jr. et al describes the oxidation of high melting point hydrocarbons using as catalysts the oxides of heavy metals of two or more valances such as nickel, lead, copper, cobalt or manganese, or the metals themselves in finely-divided form, or the soaps and resinates of these metals, such as the oleates, stearates, linoleates or linolenates. Manganese oleate is disclosed as a preferred catalyst by Labarthe, Jr. et al. As another example of the above-type of catalyst, U.S. Pat. No. 2,156,266 by Murphree et al mentions aluminum salts.

U.S. Pat. No. 2,704,294 by Morgan et al is directed to the redox catalytic liquid phase oxidation of lower aliphatic hydrocarbons. The invention of U.S. Pat. No. 2,704,294 concerns the addition of 2 to 20% on the weight of the solvent of an alkali metal or alkaline earth metal compound to the redox catalyst oxidation system to strongly inhibit oxidation beyond an intermediate point. As prior art, Morgan et al states that the use of the alkali metal and alkaline earth metal compounds in the liquid phase hydrocarbon oxidation operation in small amounts, e.g., less than 1% on the weight of the solvent, promotes or initiates the activity of oxidation catalysts such as the salts of metals such as cobalt, nickel, copper, cerium, iron, mercury, chromium, antimony, manganese, uranium, molybdenum, tungsten, tantalum, columbium, vanadium, zirconium, titanium, lead, tin, gold and silver.

U.S. Pat. No. 2,794,040 by Annable et al describes the air oxidation of microcrystalline wax with or without the presence of a catalyst. When used, the catalyst is described as an oil soluble salt of lithium, sodium, potassium, calcium, strontium, aluminum, barium, nickel, iron, cobalt, manganese, copper, zinc, molybdenum, vanadium, tungsten or chromium. A catalyst promoter, e.g., an alkaline earth metal oxide such as magnesium oxide, can be employed in small amounts, such as 0.01 to 0.5% by weight, preferably about 0.05 to 0.1%, based on feed. The catalyst is used in a concentration of about 0.1 to 2.0%, preferably about 1%, by weight of feed. Annable et al exemplify their process using 1% manganese stearate with either 0.05% or 0.1% magnesium oxide.

U.S. Pat. No. 2,808,423 by Bartlett et al employs a magnesium or calcium salt of a carboxylic acid with a manganese salt of a carboxylic acid as a catalytic combination for liquid phase oxidation of petroleum materials. Very small amounts of manganese are used. The total amount of catalyst is such that the combined manganese metal and alkaline earth metal represent 0.01 to 0.1, preferably 0.015 to 0.05 weight percent of the oxidation charge. However, the weight percent of manganese metal, based on the combined weight of manganese metal and alkaline earth metal, is in the range of 0.1 to 8.0 weight percent, preferably 1.0 to 4.0 weight percent. This means that the maximum amount of manganese metal is 0.008 parts per hundred parts, although the specific examples of Bartlett et al use only 0.0005% manganese.

In U.S. Pat. No. 2,095,473 by Keunecke, paraffinic hydrocarbons are oxidized in the presence of a catalyst consisting of a mixture of one or more compounds containing manganese with one or more compounds containing alkali metal, or consisting of one or more compounds containing manganese as well as an alkali metal. In the Example, 100 parts of a paraffin wax is oxidized in the presence of 0.18 part potassium permanganate and 0.05 part caustic potash. This corresponds to about 0.061 weight percent manganese metal and 0.35 weight percent potassium metal.

U.S. Pat. No. 2,610,974 by Nelson is directed to the oxidation of microcrystalline wax in the presence of about 0.1 to 4.0% by weight of an oxidation catalyst such as manganese salts, ammonium vanadate and potassium permanganate. Oxidation catalyst promoters or sensitizers, such as sodium carbonates, manganese palmitate or other manganese salts, can be added to the feed in small amounts, for instance in an amount equal to or less than the quantity of oxidation catalyst employed. The catalyst can be added in aqueous solution.

SUMMARY OF THE INVENTION

An object of this invention is to provide an improved process for the oxidation of hydrocarbon waxes and petrolatums containing redox metal catalyst poisons using an oxidizing gas.

Another object of this invention is to provide a process for oxidizing hydrocarbon waxes and petrolatums containing redox metal catalyst poisons more easily than has heretofore been possible.

Still another object of this invention is to provide improved hydrocarbon oxidates characterized by superior color and reduced odor, without the need of large quantities of expensive metal redox catalysts.

Another object of this invention is to provide an improved process for the oxidation of hydrocarbons not requiring an induction period while providing a controlled rate of oxidation to oxidates of high acid number.

A further object of this invention is to provide an improved process for the oxidation of hydrocarbons which contain oxidation inhibitors.

Other objects of this invention will be apparent to the skilled artisan.

In accordance with the present invention, the oxidation of hydrocarbons is carried out by blowing an oxidizing gas through a liquid or molten mass of hydrocarbons in the presence of a redox metal catalyst present in an amount significantly below that normally employed to catalyze the oxidation where used alone, and a complementary amount of an oxidation promoting alkali metal or alkaline earth metal.

In preferred embodiments of the present invention, the hydrocarbon waxes and petrolatums used as feeds contain one or more oxidation inhibitors which would normally prevent significant oxidation from occurring if the oxidation promoter was used above, that is in the absence of the redox metal catalyst.

More specifically, in the present invention, the redox metal catalyst is preferably manganese-based and the promoter is an alkaline earth metal provided in the form of its hydroxide, carbonate, halide, or other inorganic acid salt, or organic acid salt thereof.

In preferred embodiments of the present invention, the redox metal catalyst, based on redox metal content, is present in about 0.03 to 0.04 percent by weight, preferably about 0.04 percent by weight, based on weight of feed, and the weight ratio of redox metal to promoter metal is about 1:0.53 to 1:3, preferably about 1:1 to 1:2, most preferably about 1:1, with the hydrocarbon feed having an average number of carbon atoms per molecule of 20 to 100.

The oxidation is conducted under suitable conditions of gas flow, pressure and temperature to oxidize the hydrocarbon wax or petrolatum to a predetermined acid number.

DETAILED DESCRIPTION OF THE INVENTION

As disclosed hereinabove, the present invention involves the use of a combination of a redox metal catalyst and an inorganic metal promoter to efficiently oxidize various hydrocarbon waxes and petrolatums. Redox metal catalysts are well known in the field of hydrocarbon oxidation. Although favorable results are usually obtainable, a significant drawback to the use of the redox metal catalyst is its high cost.

Bearing the above in mind, it is believed that the present invention is applicable to nearly all of the prior art wax and petrolatum hydrocarbon oxidation procedures catalyzed by a redox metal catalyst. Accordingly, although the present invention will be exemplified using manganese-based redox catalysts, many of the other well known redox metal catalysts should be equally suitable for practicing this invention. For example, redox metal catalysts based on cobalt, iron, copper, chromium, lead, nickel, and the like, including combinations thereof, should be usable in practicing the benefits of this invention. These redox metals can be used in the forms in which they are employed in the prior art, generally as inorganic salts, e.g. halide, sulfate, etc., or organic acid or resinate salts, e.g. acetate, propionate, stearate, naphthenate, benzoate, etc.

Concerning the preferred manganese redox catalyst, as is known in the art, the manganese "metal" component can be provided either as a cation of a manganese salt, or in combined form as a portion of an anion. For example, the manganese based catalyst could be a manganese carboxylate or an alkali metal or alkaline earth metal permanganate, i.e., potassium, sodium or calcium permanganate.

The alkali metal or alkaline earth metal promoter can also be provided in various forms, some of which are known in the art. For example, the various hydroxides, carbonates including bicarbonates, sulfates, carboxylates and halides can be used. Also, reference is made to my co-pending application Ser. No. 245,801, filed Mar. 20, 1981, entitled "Inorganic Salt Oxidation Promoters" for additional disclosure of representative alkali metal and alkaline earth metal promoters. Although calcium carboxylates will be used in many of the examples hereinbelow, other suitable promoter compounds would be lime, NaOH, $(Ba(OH)_2$, $Al(OH)_3$, $CaCO_3$, $K_2CO_3$, $Li_2CO_3$, $BaCO_3$, $NaHCO_3$, $LiHCO_3$, $MgCO_3$, sodium or calcium formate, acetate or stearate, NaCl, $CaCl_2$, $BaCl_2$, $AlCl_3$, etc.

As disclosed above, a significant advantage of the present invention is the ability to greatly reduce the amount of expensive metal redox catalyst used in the prior art. The amount of catalyst used in the prior art would vary depending upon such factors as specific metal component, feed characteristics, reaction parameters, and the like. In general the practice of the present invention enables one to reduce the amount of needed metal catalyst down to about 1/10th or perhaps even less than that required in the prior art for equivalent feed and oxidation. Again, using manganese metal as an illustration, although it is expected that the concentration parameters set forth below would be very similar for other redox metals, prior art oxidation of waxes and petrolatums to acid number in the area of 30 to 60 have often required about 0.4 to 2.5 weight percent of manganese metal based on feed. With the practice of the present invention, the amount of manganese metal can be reduced down to about 0.04 weight percent and less, based on weight of feed.

The amount of alkali metal or alkaline earth metal promoter employed is calculated based on concentration of redox metal. On a metal to metal basis, the weight ratio of redox "metal" to promoter "metal", preferably calcium, will be about 1:0.53 to 1:3, preferably about 1:1 to 1:2, most preferably about 1:1.

In my parent application Ser. No. 262,859, I disclosed laboratory results and broader ranges of redox metal and promoter metal (0.006 to 0.04 percent by weight redox metal and weight ratio of redox metal to promoter metal of about 0.2:1 to 5:1). In my parent application, many laboratory runs were included as examples, including a run in Example 1 where the ratio of redox metal to promoter metal is 1:3 (0.063 percent manganese CEM-ALL containing 12% manganese and 0.313 percent calcium CEM-ALL containing 8% calcium), and a run in Example 2 using 0.03% redox metal with a redox metal to promoter metal ratio of about 1:0.53 (0.250 percent of the 12 percent manganese CEM-ALL with 2% of a calcium soap containing 0.8 percent calcium).

In the present invention, the redox catalyst and promoter metals are preferably added to the hydrocarbon feed in the form of compounds such as salts, hydroxides and the like which are readily dispersible therein. For example, the various metal carboxylates and resinates, such as the carboxylates of from 1 to about 16 carbon atoms, the benzoates and the naphthenates, could be used. The various CEM-ALL LIQUIDS available from Mooney Chemicals, Inc. of Cleveland, Ohio, can be useful to practice the present invention since they are hydrocarbon soluble liquids containing from about 4% to 20% or so of the metal as carboxylates, believed to be a mixture of $C_8$ and $C_{10}$ branched chain carboxylic acids. Where the redox catalyst and/or promoter compound are water-soluble, they can be added in the form of water solution. Hydrocarbon dispersible slurries of the catalyst and/or promoter are usable, such as a water-lime slurry as promoter.

Another important attribute of the present invention is that the hydrocarbon feed contains oxidation inhibitors which would usually significantly retard the use of the promoter compound alone to initiate the oxidation reaction. Quite often, these oxidation inhibitors are sulfur or nitrogen-based compounds naturally occurring in the hydrocarbon feed.

The hydrocarbons useful in this process include the conventional feedstocks used as oxidizer feedstock. Ordinarily, such a feedstock comprises a mixture of saturated hydrocarbons having an average number of carbon atoms per molecule of 20 to 100, often 25 to 50. Waxes and petrolatums from crude oil refining, hydrocarbon mixtures from lubricant plants and the like are examples of suitable feedstocks. The present invention has been found to be particularly useful with feedstocks of about $C_{44}$ to $C_{65}$ or higher petrolatums containing oxidation inhibitors.

Ordinarily, the process will be carried out as a batch process. Air or another oxidizing gas is forced through the reaction mixture of hydrocarbon redox catalyst and promoter compound at a rate of between 0.5 and 10 liters, preferably 3.5 to 4.0 liters (measured at 760 mm of mercury and 25° C.) per liter of hydrocarbon per minute at a temperature of between 150° and 180° C., preferably 160° to 165° C. Ordinarily, the temperature will rise as the oxidation proceeds so that only minimal heat may be required for the oxidation. The oxidation process is conducted at a pressure of between 50 and 400 psig (4.4–28.2 atmospheres), preferably 150 to 250 psig. The process is discontinued when a desired acid number is reached. The term "acid number" is defined to mean the number of milligrams of potassium hydroxide required to neutralize 1 gram of sample. Generally, the reaction will be carried out for about 0.25 to 10 hours, preferably about 1 to 5 hours to reach a predetermined acid number.

EXAMPLE

A number of air oxidations were conducted in a commercial plant scale 2200 gal. reactor. In each case, the reactor charge amounted to approximately 1270 gal. (9142 lbs.) of hydrocarbon feed. The hydrocarbon material was a mixture of oxidizer feeds and contained predominantly petrolatums and petrolatum-like substances all of which contained some naturally-occurring oxidation inhibitors. To the hydrocarbon feed there was added the amounts of manganese catalyst and lime slurry as shown in the accompanying table. For Run No. 44 in the table, for example, 3½ gal. (30.2 lbs.) of manganese catalyst (0.33% by weight) and a lime-water slurry containing 7½ lbs. (0.08% by weight) of lime and approximately 14 lbs. (0.15% by weight) of water were added to the hydrocarbon charge. The reaction conditions were approximately 2 hours for these reactions at a temperature of approximately 310°–330° F., a pressure of about 200–210 psig and an air input rate of about ½ standard cubic foot of air per minute per gal. of charge (measured at 25° C. and one atmosphere). Acid number determinations were made at the end of each run. One objective of these runs is to obtain at least a 45–50 acid number in two hours or less.

TABLE I

EVALUATION OF (Mn CEM-ALL-LIME) CATALYST SYSTEM

| RUN | Mn CEM-ALL (%) | LIME (%) | WATER (%) | A.N. | REMARKS |
|---|---|---|---|---|---|
| 26 | 0.66 | None | None | 48.6 | Good run |
| 28 | 0.16 | 0.16 | 0.31 | 52.6 | Sluggish |
| 29 | 0.33 | 0.16 | 0.31 | 46.2 | Good run |
| 30 | 0.33 | 0.16 | 0.31 | 48.4 | Good run |
| 31 | 0.33 | 0.11 | 0.21 | 48.1 | Excellent run |
| 32 | 0.33 | 0.05 | 0.10 | 48.6 | Excellent run |
| 33 | 0.16 | 0.05 | 0.10 | 49.4 | Sluggish |
| 34 | 0.16 | 0.03 | 0.06 | 19.4 | Sluggish |
| 35 | 0.25 | 0.05 | 0.10 | 48.2 | Excellent run |
| 36 | 0.25 | 0.05 | 0.11 | 48.8 | Excellent run |
| 37 | 0.25 | 0.05 | 0.10 | 48.1 | Excellent run |
| 38 | 0.21 | 0.05 | 0.10 | 48.8 | Sluggish |
| 39 | 0.25 | 0.05 | 0.10 | 42.6 | Sluggish |
| 40 | 0.33 | 0.11 | 0.21 | 49.2 | Excellent run |
| 41 | 0.33 | 0.11 | 0.20 | 45.3 | Excellent run |
| 42 | 0.33 | 0.08 | 0.15 | 48.2 | Excellent run |
| 43 | 0.25 | 0.08 | 0.15 | 23.8 | Sluggish |
| 44 | 0.33 | 0.08 | 0.15 | 49.0 | Excellent run |
| 45 | 0.33 | 0.08 | 0.15 | 45.9 | Excellent run |
| 46 | 0.33 | 0.08 | 0.14 | 49.4 | Excellent run |
| 47 | 0.33 | 0.08 | 0.15 | 46.2 | Excellent run |
| 48 | 0.33 | 0.08 | 0.15 | 48.9 | Excellent run |
| 49 | 0.33 | 0.08 | 0.15 | 49.4 | Excellent run |
| 50 | 0.33 | 0.08 | 0.15 | 48.4 | Excellent run |
| 51 | 0.33 | 0.05 | 0.10 | 47.1 | Sluggish |
| 52 | 0.25 | 0.08 | 0.16 | 48.2 | Excellent run |
| 53 | 0.33 | 0.08 | 0.15 | 47.7 | Excellent run |
| 54 | 0.33 | 0.08 | 0.14 | 47.5 | Excellent run |
| 55 | 0.33 | 0.08 | 0.15 | 46.7 | Excellent run |
| 56 | 0.33 | 0.08 | 0.15 | 47.8 | Excellent run |
| 57 | 0.33 | 0.08 | 0.15 | 48.2 | Excellent run |
| 58 | 0.33 | 0.08 | 0.15 | 47.4 | Excellent run |
| 59 | 0.33 | 0.08 | 0.16 | 46.1 | Excellent run |
| 60 | 0.33 | 0.08 | 0.15 | 47.8 | Excellent run |
| 61 | 0.33 | 0.08 | 0.15 | 46.4 | Excellent run |
| 62 | 0.33 | 0.08 | 0.14 | 48.4 | Excellent run |
| 63 | 0.33 | 0.08 | 0.15 | 46.2 | Excellent run |
| 64 | 0.33 | 0.08 | 0.15 | 48.0 | Excellent run |
| 65 | 0.33 | 0.08 | 0.15 | 56.2 | Excellent run |
| 66 | 0.33 | 0.08 | 0.15 | 49.1 | Excellent run |

From Table I it is seen that excellent results were consistently obtained using 0.33% manganese CEM-ALL (12% Mn) and 0.08% lime, these values corresponding to 0.040% by weight Mn content and 0.043% by weight Ca. Manganese CEM-ALL (12%) concentrations of 0.21% or less (corresponding to 0.025% by weight Mn) produced consistently sluggish results.

Higher levels of lime, i.e., a calcium:manganese ratio of 2.8:1 (about 3:1), tend to suppress manganese activity in the initiation step and low lime levels, i.e., less than 1:1 may prove inadequate for suitable oxidation propagation.

The runs of the Example were carried out in an oxidizer used in a commercial plant where an initiation exotherm is normally used to achieve reaction initiation peak temperature rather than only heating. CEM-ALL contains a mineral spirits base which provides a rapid initiation exotherm. Otherwise, additional heat input would be required.

Variations of the invention will be apparent to the skilled artisan.

I claim:

1. A process for oxidizing a liquid mixture of saturated hydrocarbons having an average number of carbon atoms per molecule of 25 to 50 and containing at least one of an oxidizing inhibitor and redox metal catalyst poison to an acid number of up to at least about 45 to 50 comprising blowing air at a rate of 3.5 to 4.0 liters per minute per liter of hydrocarbons through a liquid mass of said hydrocarbons containing at least one of an oxidation inhibitor and redox metal catalyst poison in the presence of 0.03 to 0.04 percent by weight of manganese provided by manganese carboxylate, based on weight of said liquid hydrocarbons; and an oxidation promoting amount of calcium provided by water-lime slurry, the weight ratio of manganese to calcium being about 1:1 to 1:2;

the temperature of reaction being 160° C. to 165° C., the pressure being 150 to 250 psig and the reaction being carried out for about 2 hours or less, thereby providing an oxidized hydrocarbon mixture having an acid number of at least about 45 to 50.

2. The process of claim 1 wherein said weight ratio of manganese to calcium is about 1.1.

* * * * *